(12) United States Patent
Chang et al.

(10) Patent No.: US 6,224,542 B1
(45) Date of Patent: *May 1, 2001

(54) ENDOSCOPIC CAMERA SYSTEM WITH NON-MECHANICAL ZOOM

(75) Inventors: William H. L. Chang, Milpitas; Markus Yap, Santa Clara; Salmaan Hameed; Richard A. Beutter, both of San Jose, all of CA (US)

(73) Assignee: Stryker Corporation, Kalamazoo, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/226,050

(22) Filed: Jan. 4, 1999

(51) Int. Cl.$^7$ .................................................. A61B 1/04
(52) U.S. Cl. ......................... 600/109; 600/118; 600/168
(58) Field of Search ..................... 600/103, 109, 600/117, 118, 168, 921; 348/74, 65, 82–85; 396/57, 374

(56) References Cited

U.S. PATENT DOCUMENTS

| | | | |
|---|---|---|---|
| 4,891,697 | * 1/1990 | Saito et al. | 348/65 |
| 4,989,253 | * 1/1991 | Liang et al. | 128/897 |
| 5,261,404 | * 11/1993 | Mick et al. | 600/425 |
| 5,572,999 | * 11/1996 | Funda et al. | 600/118 |
| 5,815,640 | 9/1998 | Wang et al. | |
| 5,836,869 | * 11/1998 | Kudo et al. | 600/118 |
| 5,876,325 | * 3/1999 | Mizuno et al. | 600/118 |
| 5,910,801 | * 6/1999 | Rosenburg et al. | 345/339 |
| 5,945,985 | * 8/1999 | Babin et al. | 345/302 |

FOREIGN PATENT DOCUMENTS 9609587   3/1996   (WO).
9749340   12/1997  (WO).

OTHER PUBLICATIONS

Product Information, "The Operating System for the Operating Room", HERMES™ downloaded from http://www-.computermotion.com/hermes.htm on Nov. 16, 1998, 2 pages.

Press release, "Computer Motion, Inc. Brings Complete Offering of Hermes–Ready™ Medical Devices to the Operating Room", Contact: Stephen L. Wilson, Computer Motion, Inc., Oct. 26, 1998, Santa Barbara, CA, downloaded from http://www.computermotion.com/pressr53.htm, 2 pages.

Sackier, M.D., et al., "Robotic's Application in Surgery; Voice Activation of a Surgical Robotic Assistant", *The American Journal of Surgery*, vol. 174:406–409, Jan. 30, 1997.

News article, "Zeus Robotic Surgical System Enables Endoscopic Coronary Anastomosis On a Beating Heart Through Incisions Smaller than the Diameter of a Pencil", downloaded from http://my.excite.com/news/bw/981110/computer–motion on Nov. 16, 1998.

* cited by examiner

*Primary Examiner*—John P. Leubecker
(74) *Attorney, Agent, or Firm*—Blakely, Sokoloff, Taylor & Zafman, LLP

(57) ABSTRACT

An endoscopic camera system includes zooming capability to non-mechanically enlarge images of internal features of a body during an endoscopic procedure. The system includes a scope for insertion into the body, a camera head coupled to the scope, and a camera control unit coupled to the camera head. Video image data of internal features of the body are acquired through the scope by the camera head and transmitted to the camera control unit, which generates video images for display on a monitor. The camera control unit includes zoom circuitry for digitally zooming the video images in real-time. Operation of the zoom circuitry may be controlled by manual input or by voice commands. Voice commands may be used to set and recall preset zoom views.

22 Claims, 6 Drawing Sheets

ENDOSCOPIC CAMERA SYSTEM WITH NON-MECHANICAL ZOOM

FIELD OF THE INVENTION

The present invention pertains to the field of medical devices. More particularly, the present invention relates to endoscopic camera systems.

BACKGROUND OF THE INVENTION

Endoscopy is a medical field which allows the acquisition of high-quality video images of internal features of a human body, without the need for invasive surgery. A basic tool of endoscopy is an endoscopic camera system, which includes a scope that is inserted into the body of a patient. Some endoscopic procedures involve the use of a flexible scope, as in the field of gastroenterology, for example. Other procedures, such as arthroscopy or laparoscopy, involve the use of a rigid scope. The scope is normally connected to a camera head that includes electronics for acquiring video image data through the scope.

The connected scope and camera head may be held and manipulated during endoscopic surgery by a human surgical assistant or by a holding tool, such as a robotic positioning system. The scope has optical properties which allow it to introduce light into the body of the patient and to transmit light from the body cavity to the camera head. A high intensity light source may be coupled to the scope by a fiber optic cable to introduce light into the body. The camera head is coupled through a flexible transmission line to a camera control unit, which is often mounted on a mobile cart. The control unit processes video data provided by the camera head to generate images, which are displayed on a video monitor. The control unit may also be coupled to various peripheral devices, such as a printer and a video cassette recorder (VCR).

During endoscopic surgery, the surgeon sometimes requires a more close-up ("zoomed") view of a feature inside the body. One way of accomplishing this is for the person or machine holding the scope to physically move the scope closer to the feature of interest. This approach has several disadvantages, however. For example, physically moving the scope consumes valuable time during surgery while the scope is repositioned. The repositioning process may involve several trial-and-error steps as the scope holder makes corrections in response to verbal feedback from the surgeon. It may be difficult for a human holder to maintain the scope in precisely the desired position, particularly when fatigue sets in. Further, moving the scope closer to the object of interest might interfere with the surgeon's ability to operate.

Some endoscopic camera systems provide the capability to zoom in on an object without having to move the scope closer to the object. Such systems use mechanical zooming, which generally involves adjusting the configuration of optics within the scope and/or its connection to the camera head. This may be done manually, such as by turning a knob or coupler, or electronically by pressing a button or other appropriate control. However, even these systems require time to adjust and are subject to a certain amount of trial-and-error in zooming.

Another problem is that zooming reduces the field of view of the scope. The scope has a maximum field of view corresponding to its non-zoomed setting. As the scope zooms in on an object, features that were near the periphery of the field of view may become lost outside the field of view. Consequently, the surgeon undesirably loses view of the general field of surgery within the body. Reacquiring the more general view requires reverting to a lower magnification setting. Thus, it is desirable to have an endoscopic camera system which overcomes these and other disadvantages of the prior art.

SUMMARY OF THE INVENTION

An endoscopic camera system includes the capability to receive image data from an endoscopic camera and to process the image data to generate images, including the capability to non-mechanically zoom images. Particular embodiments of the endoscopic camera system may also include the capability to control zooming in response to voice commands.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

An endoscopic camera system having digital zoom operable in response to voice commands is described. As will be described in greater detail below, the endoscopic camera system includes a camera control unit having zoom circuitry for non-mechanically zooming video images of internal features of the body in real-time. Operation of the zoom circuitry may be controlled by manual user input or by voice commands. The digital zoom feature avoids the need for a person to move the scope back and forth to obtain a closer view of an organ or other feature. Because zooming is done digitally, the endoscope can remain stationary (e.g., held by a robotic device or other tools), thus avoiding waste of surgery time in repositioning the scope. In addition, zoomed views of certain target areas can be pre-defined, stored in memory, and then recalled instantly during surgery when needed. The surgeon can easily and virtually instantaneously switch between zoomed views with a voice command or the touch of a manual control. Further, one or more zoomed views can be displayed within the overall field of view in a picture-in-picture format.

Figure 1:
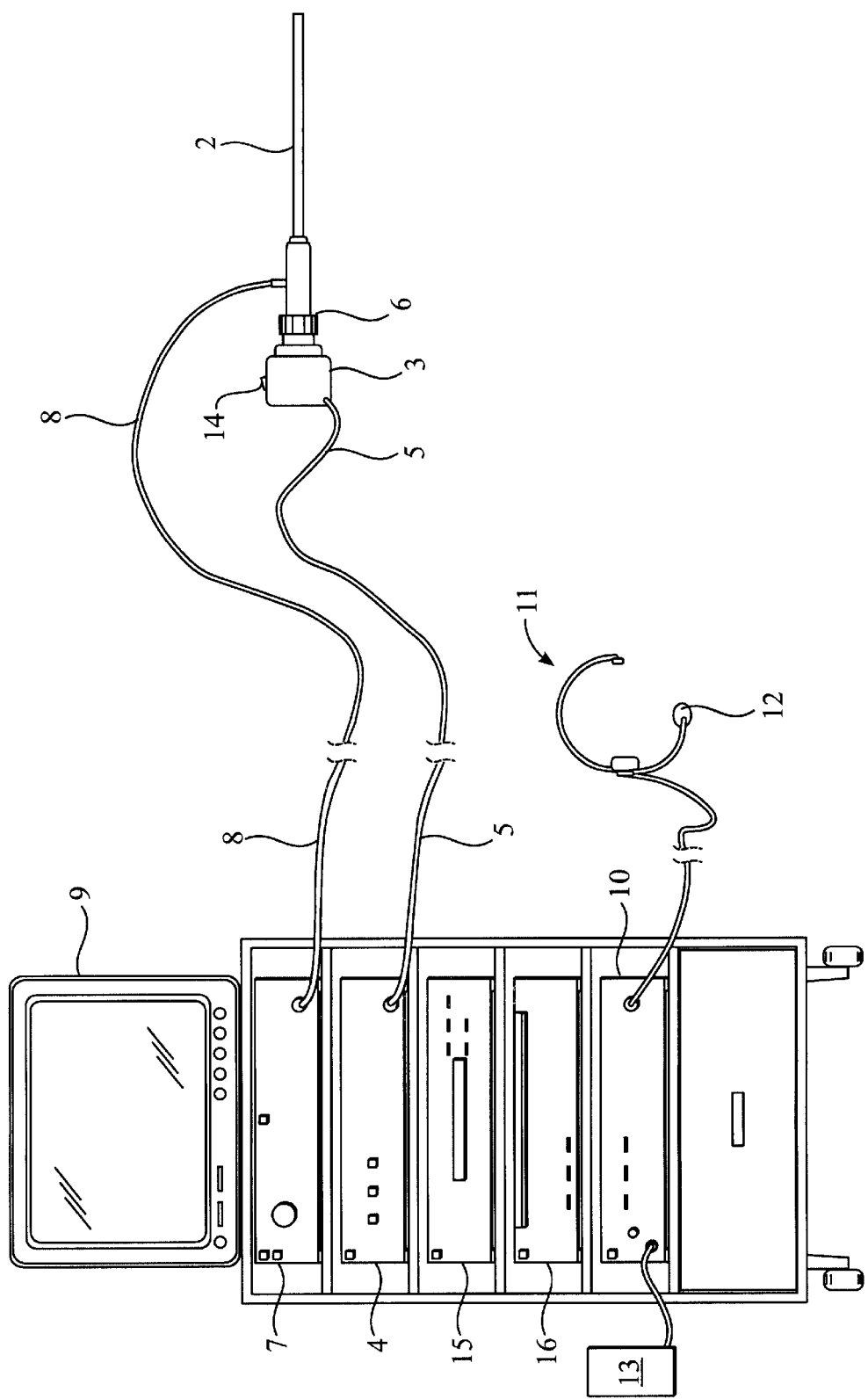
FIG. 1 illustrates an endoscopic camera system.

FIG. 1 illustrates an endoscopic camera system in which the present invention may be implemented. The illustrated camera system includes a rigid scope 2 of the type that is commonly used for laparoscopy or arthroscopy. The scope 2 is coupled to a camera head 3 by a coupler 6. The camera head 3 includes well-known circuitry, such as chargecoupled devices (CCDs), for acquiring color video image data of internal features of the body through a system of lenses within the scope 2. Light is provided to the scope 2 by a flexible light source 7 through an appropriate flexible light conduit 8, such as a fiber optic cable. The camera head 3 is coupled to a camera control unit (CCU) 4 by a flexible transmission line 5. Operation of the camera system is controlled, in part, from CCU 4. Transmission line 5 conveys video image data from the camera head 3 to the CCU 4 and conveys various control signals bi-directionally between the camera head 3 and the CCU 4. It is assumed, for purposes of this description, that image data output by the camera head 3 onto transmission line 5 are in an analog format, such as National Television Standards Committee (NTSC) format. However, in alternative embodiments, the image data output by the camera head 3 may be digital, in which case transmission line 5 may be Firewire, Universal Serial Bus (USB), or another type of high-speed digital interface.

A button or other similar manual control 14 on the camera head 3 allows a user to control zooming and/or other functions of the camera system. Zooming and other functions may also be controlled by voice commands using a voice response control system (VCS) 10, which is coupled to the CCU 4. Voice commands are input into a microphone 12 on a headset 11 worn by the surgeon and coupled to the voice control response system (VCS) 10. VCS 10 employs speech-recognition techniques to generate control signals in response to the voice commands. A handheld control device (pendant) 13 is coupled to the VCS 10 as an alternative means of operating certain functions of the VCS 10. Also coupled to the CCU 4 are a video cassette recorder (VCR), a printer 16, and (optionally) other devices (not shown), as desired. Video image data acquired by camera head 3 and processed by CCU 4 is converted to images, which can be displayed on monitor 9, recorded in VCR 15, and/or used to generate static images, hard copies of which can be produced by printer 16.

Figure 2:
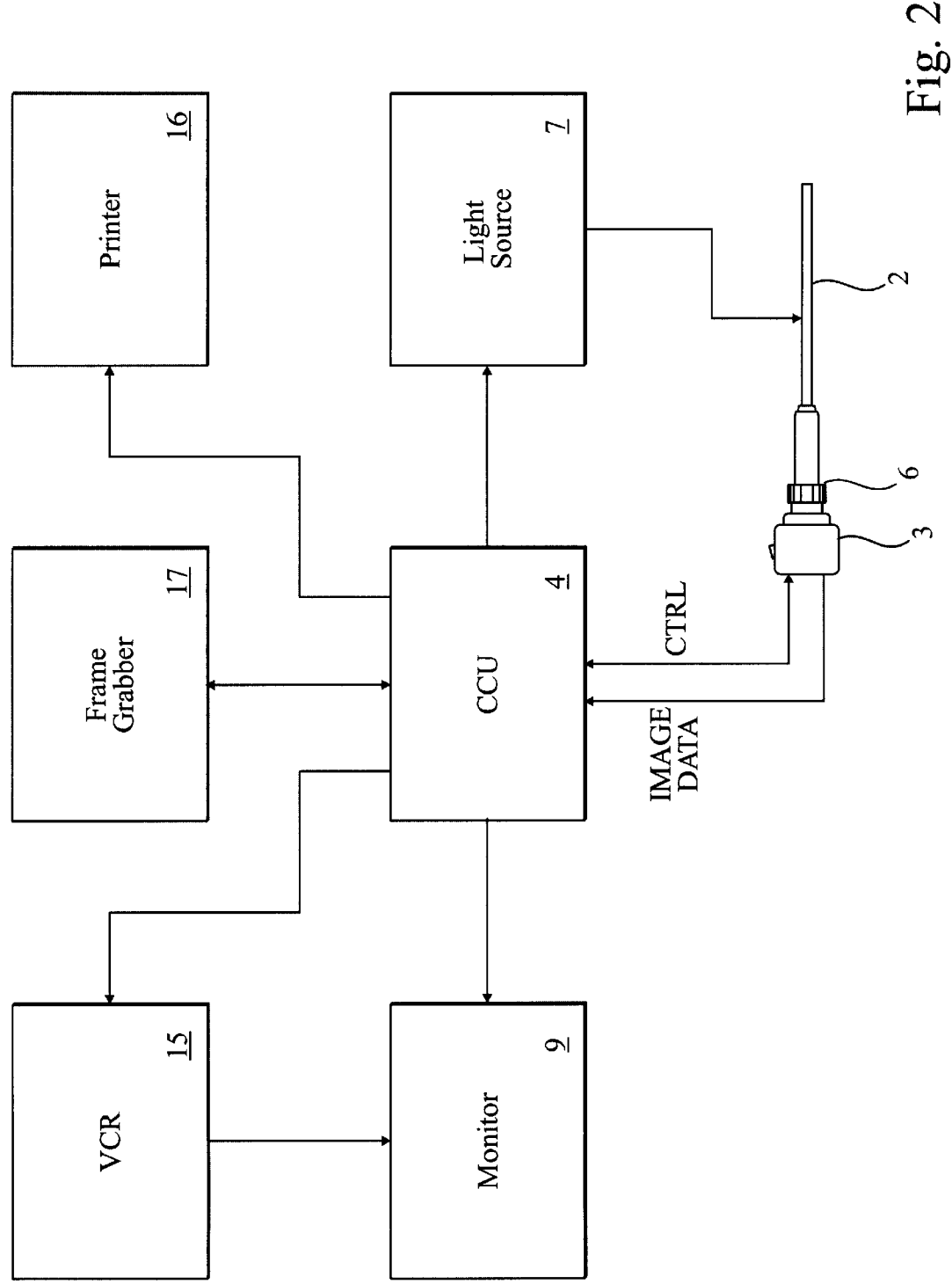
FIG. 2 is a block diagram of the endoscopic camera system of FIG. 1.

FIG. 2 is a block diagram of the endoscopic camera system of FIG. 1, according to one embodiment. The CCU 4 includes user input controls for adjusting various settings of the camera system, such as shutter, gain, and white balance. The camera head 3 is coupled to the CCU 4 so as to allow communication of both image data and control signals between CCU 4 and camera head 3. Also coupled to the CCU 4 are the light source 7, monitor 9, VCR 15, printer 16, and frame grabber 17. Frame grabber 17 may be used to capture and save individual frames of video data acquired from camera head 3, which may then be printed on printer 16.

Note that numerous variations upon the embodiment in FIG. 2 may be implemented as alternative embodiments. In one alternative embodiment, for example, the frame grabber 17 is capable of controlling other components in the system (e.g., the printer 16, VCR 15 and/or monitor 9) in response to the CCU 4; this embodiment eliminates the need for some of the illustrated connections between the CCU 4 and these other components. Also, as indicated above, other components may be added to the system, if appropriate.

As noted above, the VCS 10 (FIG. 1) can be used to operate various functions of the endoscopic camera system, including digital zooming. Techniques for recognizing speech and controlling devices in response to speech, such as may be employed by the VCS 10, are well-known in the art and therefore do not need to be described herein. Nonetheless, speech recognition and related control techniques such as may be implemented by the VCS 10 are described in International Application Under the Patent Cooperation Treaty (PCT), number WO 96/09587, entitled "A Speech Interface for an Automated Endoscopic System," filed on Sep. 21, 1995 and published on Mar. 28, 1996, which is incorporated herein by reference. Endoscopic camera systems equipped with certain voice response functions are also commercially available, such as the Stryker 882 TE Camera System with HERMES Voice Control, which is available from Stryker Endoscopy of Santa Clara, Calif., and which implements HERMES speech recognition techniques of Computer Motion, Inc., of Goleta, Calif.

Figure 3:
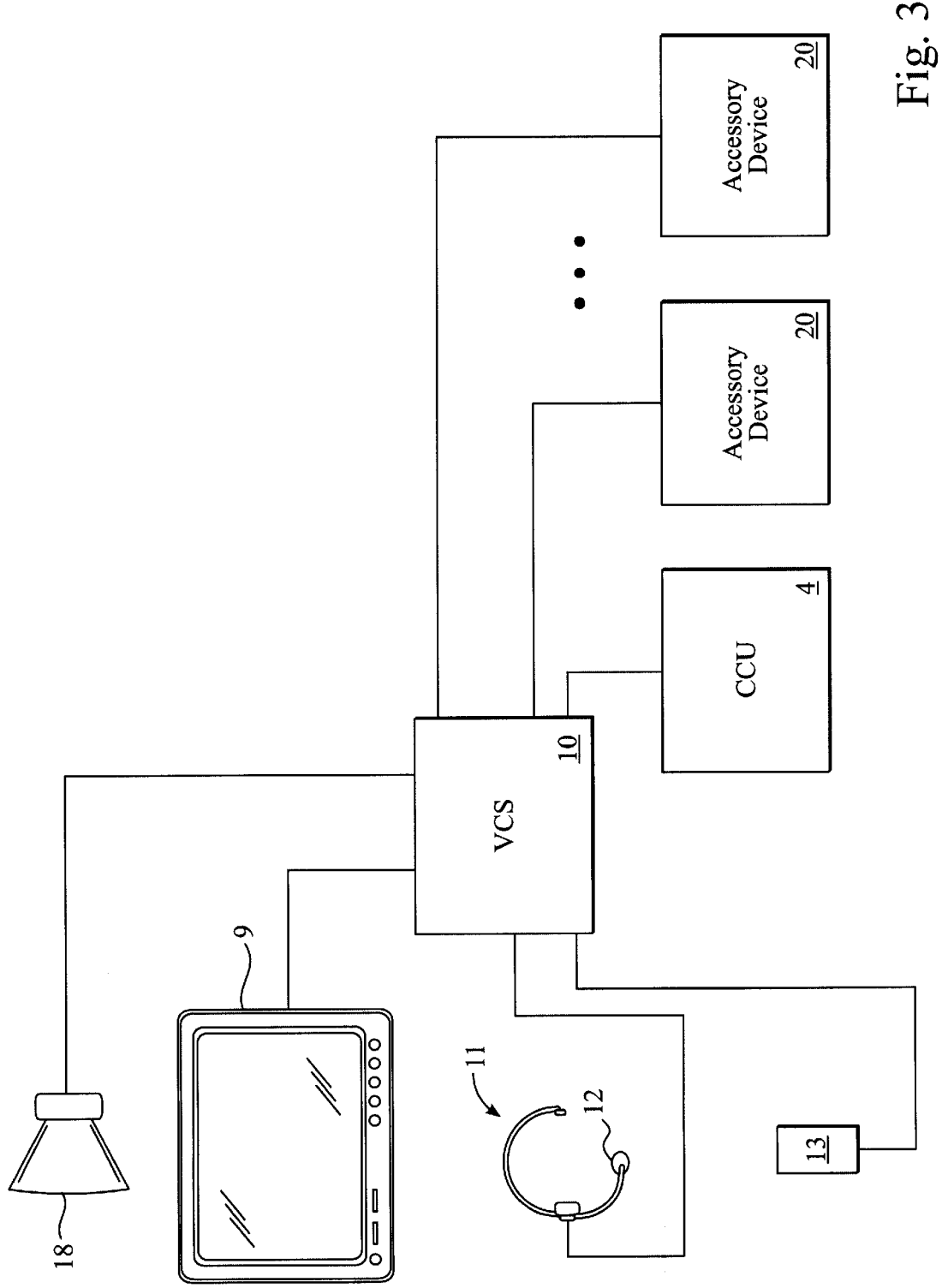
FIG. 3 is a block diagram showing a voice response control system (VCS) integrated with the endoscopic camera system.

FIG. 3 illustrates how the VCS 10 may be connected in the endoscopic camera system, according to one embodiment. In the illustrated embodiment, the VCS 10 is coupled to monitor 9 and audio speaker 18. Audio speaker 18 may be an integral component of monitor 9. The CCU 4 and (optionally) various other devices 20 are coupled to the VCS 10 by a conventional communication link/protocol, such as USB, CAN bus (ISO 11898), RS-232, or the like. (Not shown in FIG. 3 are peripheral devices that are coupled directly to the CCU 4, such as shown in FIG. 2.) Note that various configurations may be used to connect components to the VCS 10, including point-to-point connections (as shown) or a daisy chain, for example.

Figure 4:
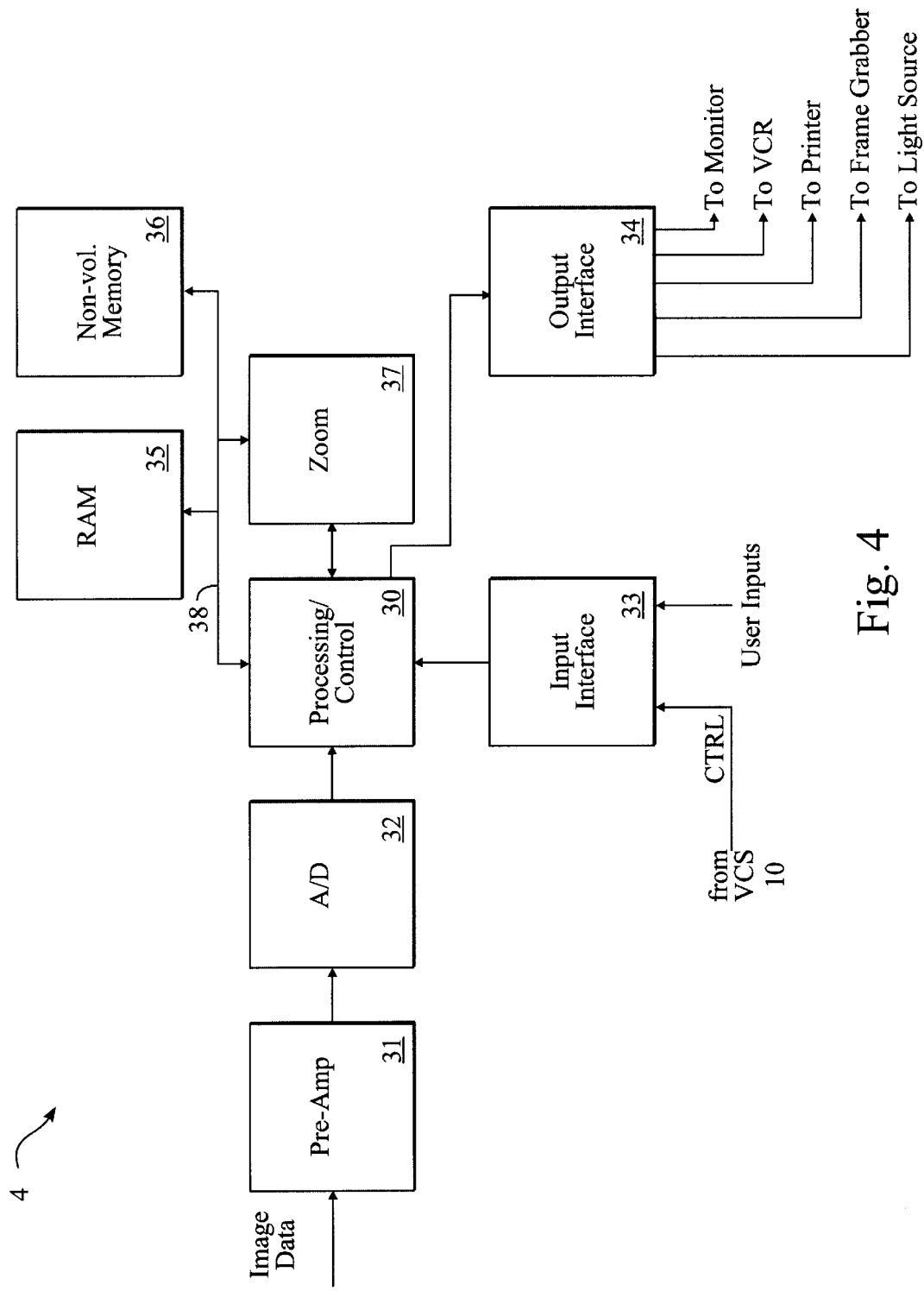
FIG. 4 is a block diagram of the camera control unit (CCU) of the endoscopic camera system.

FIG. 4 is a block diagram of the CCU 4, according to one embodiment. In the illustrated embodiment, the CCU 4 includes a processing/control unit 30, a pre-amplification stage 31, an analog-to-digital (A/D) converter 32, an input interface 33, an output interface 34, a random access memory (RAM) 35, a nonvolatile memory 36, and a zoom unit 37. Processing/control unit 30 controls the overall operation of the CCU 4 and performs signal processing, including functions commonly used in generating displayable video images. Accordingly, processing/control unit 30 may be, or may include, a general- or special-purpose microprocessor, such as a digital signal processor (DSP), application specific integrated circuit (ASIC), field programmable gate array (FPGA), or other appropriate device or combination of such devices. Software instructions executable by processing/control unit 30 for performing various functions of the CCU 4 may be stored in RAM 35, nonvolatile memory 36, or both.

During operation of the camera system, image data generated by the camera head 3 are received (via transmission line 5) by pre-amplification stage 31, where the data undergo amplification and appropriate signal conditioning. The amplified and conditioned data are then converted to digital form by A/D converter 32 and provided to processing/control unit 30. Of course, in an embodiment in which the camera head 3 outputs digital data, the A/D converter 32 would be unnecessary.

User inputs from manual controls on the CCU 4 and the camera head 3 are input to input interface 33. In addition, control signals resulting from processed and recognized voice commands from VCS 10 are also received by input interface 33. The input interface 33 then provides these signals, after any appropriate buffering and/or signal conditioning, to processing/control unit 30. In the illustrated embodiment, processing/control unit 30 generates various outputs directed to the light source 7, monitor 9, VCR 15, printer 16, and/or frame grabber 17 via the output interface 34, which performs any appropriate buffering and/or signal conditioning.

Image data may be stored at various stages of processing in RAM 35, nonvolatile memory 36, or both, which are coupled to processing in control unit 30 by a bus 38 or any other suitable type of connection. Nonvolatile memory 36 may be any device suitable for storing relatively large amounts of data, such as: read only memory (ROM), which may be programmable and erasable; flash memory; an optical, magnetic or magneto-optical (MO) mass storage device; or a combination of such devices.

The zoom functions of the present invention are provided by zoom unit 37. Zoom unit 37 generally includes circuitry for non-mechanically (digitally) zooming images generated by processing in control unit 30 in real-time (as the image data are acquired) using data acquired from the camera head 3. For purposes of this description, "non-mechanical" zooming means zooming that does not require physical manipulation of the optical properties of the camera system or repositioning of the scope, or zooming solely through the manipulation of data. Zoom unit 37 may be, or may include, a general- or special-purpose microprocessor, ASIC, FPGA, or other appropriate device or combination of such devices. Note that electronic components capable of enlarging images by manipulating data are commercially available. Such components may employ, for example, pixel and/or line interpolation to enlarge images. One such component which may be suitable for this purpose is the IP00C702 SXGA Expansion/Reduction LSI from Sumitomo Metal Industries, Ltd., which has sales offices in Saddlebrook, N.J., and Santa Clara, Calif.

Zoom unit 37 is preferably capable of enlarging images by many different, user-selectable magnification (zoom) factors. In one embodiment, zoom unit 37 is configured to zoom images according to a user's selection of any of 64 increments between a zoom factor of 1.0 (no zoom, actual size) and a zoom factor of 2.0 (twice actual size). As noted above, zooming may be controlled via a manual control, such as control 14 on camera head 3 (FIG. 1) or a manual control on the CCU 4. Zooming may also be controlled in response to voice commands input to the VCS 10 via microphone 12.

Thus, the digital zoom feature of the present invention avoids the need for a person to move the scope back and forth to focus on an organ or a feature of interest. The endoscope can remain stationary (e.g., held by a robotic device or other tool) while zooming is done digitally, thus avoiding waste of surgery time and avoiding visual disorientation of the surgeon from target organs or target areas. In addition, prior to performing a surgical procedure, the surgeon can look at the overall camera field of view and use the zoom feature to determine subsets of the field of view, i.e., "microviews", as target areas, such as the gall bladder or the bile ducts. The surgeon's selections can then be stored in memory in the CCU 4 and can then be recalled instantly during surgery through manual or voice control.

In addition, one or more zoomed views can be displayed within the overall field of view in a picture-in-picture fashion. Specifically, the digital zoom feature allows multiple zoomed views to be concurrently created in real-time by operating upon different subsets of the data representing the overall field of view. The surgeon may use voice, a joystick, or other control device to focus on a new target of interest and its corresponding field of view. Further, the surgeon can easily and virtually instantaneously switch between views and between zoom levels with a voice command or the touch of a manual control. Consequently, the surgeon is less likely to lose his or her bearings than with prior art zoom techniques. The zoom unit 37 further provides the capability to automatically zoom in or out by multiple zoom increments in response to a single user input. In that case, zooming in or out may be performed at preset rate, such as one increment per second.

Figure 5:
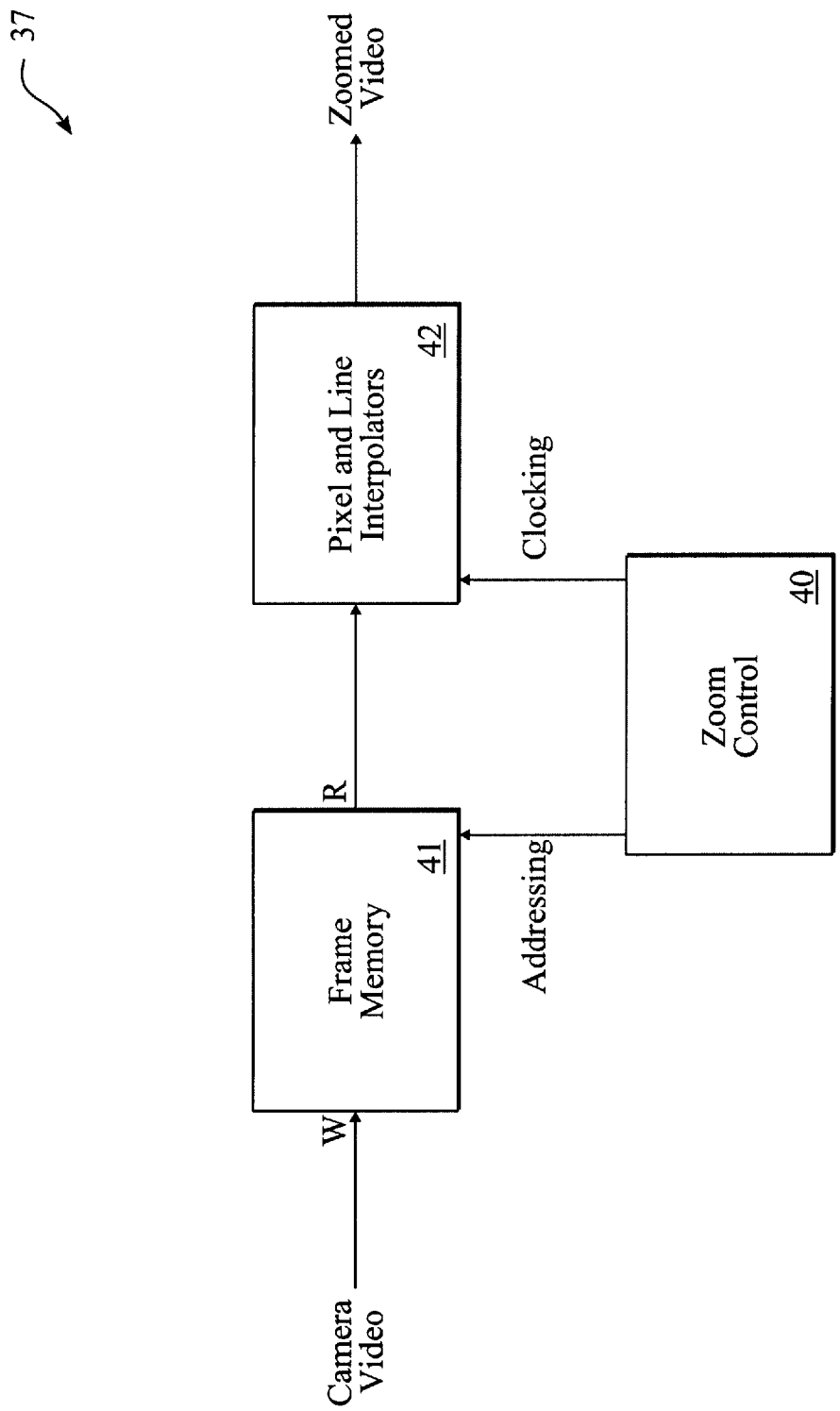
FIG. 5 is a block diagram of the zoom circuitry in the camera control unit (CCU).

FIG. 5 illustrates a functional block diagram of the zoom unit 37, according to one embodiment. As shown, the zoom unit 37 includes a zoom control circuit 40, a frame memory 41, and pixel and line interpolators 42. The zoom control unit 40 provides addressing signals to frame memory 41 and clocking signals to pixel and line interpolators 42 to control zooming functions. Zoom unit 37 may employ interpolation of pixels and/or lines or any other suitable technique for enlarging images in real-time through the manipulation of data. Hence, video image data are input to the frame memory 41. Zoom unit 37 may receive the data from storage in RAM 35 or nonvolatile memory 36, or from processing and control unit 30. Accordingly, in response to the addressing and clocking signals image data is read from frame memory 41 to the pixel and line interpolators 42 where interpolation takes place. Processed video data representing zoomed images is then output by pixel and line interpolators 42 onto bus system 38, for storage in RAM 35 or non-volatile memory 36 and/or for transmission to other system components, such as the monitor or VCR.

Figure 6:
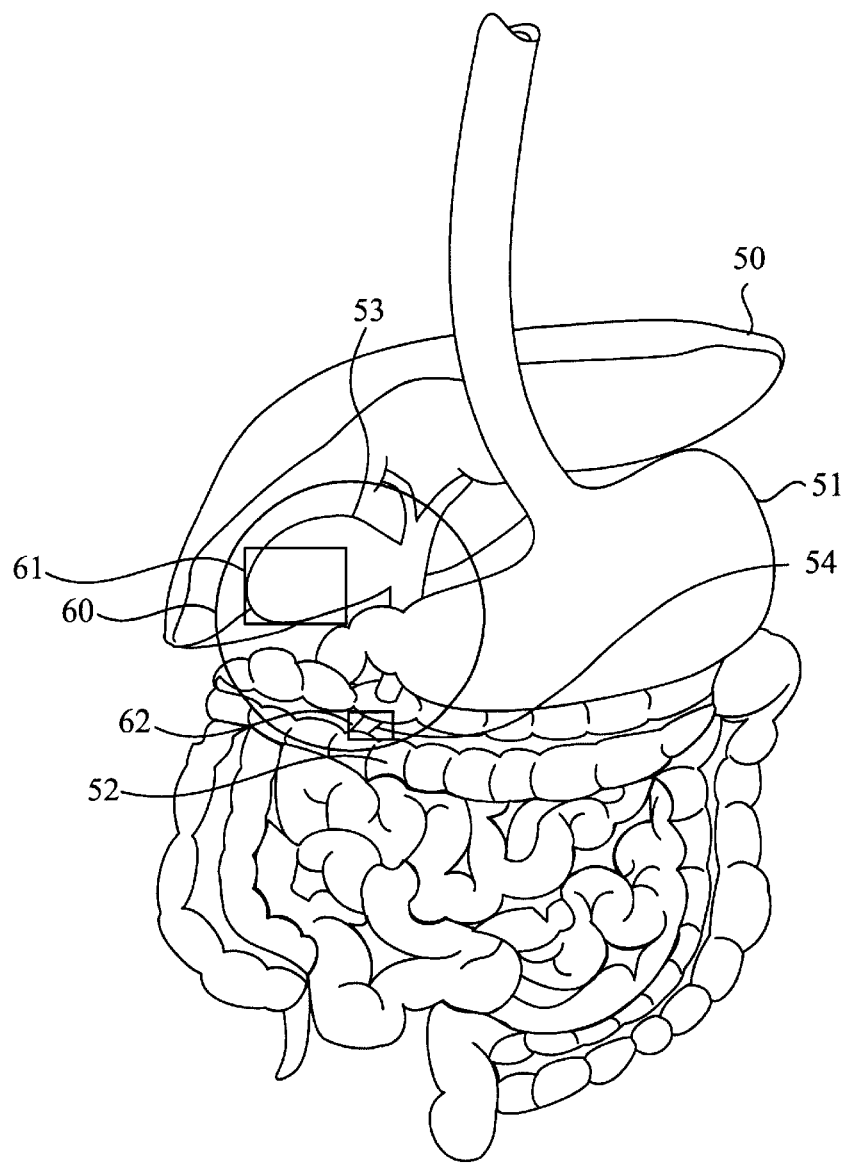
FIG. 6 illustrates internal organs of a human body and various zoom views that can be generated using the present invention.

Referring now to FIG. 6, an example of how the digital zoom feature may be used to advantage is now described. FIG. 6 shows internal features of a human body, including the liver 50, the stomach 51, the small intestine 52, the gall bladder 53, and the bile duct 54. Circle 60 corresponds to the general field of view of the camera system, i.e., the field of view corresponding to a non-zoomed image. The surgeon may preselect various zoomed views, such as view 61 of the gall bladder 53 or view 62 of the bile duct 54. Zoomed views 61 and 62 and other zoomed view may be displayed in full-screen format on the monitor. Alternatively, as noted above, one or more zoomed views may be displayed on the monitor in a picture-in-picture manner within the non-zoomed view.

Using the VCS 10, the surgeon can name preselected target areas and save selections, including parameters such as field of view, shutter setting, gain, and lighting levels, for future voice activation during surgery. For example, the gall bladder view 61 can be stored under the name "Gall bladder", which the surgeon can simply speak into the microphone 12 during surgery to obtain this view. Similarly, the term "Macro" may be used, for example, to instantly view the overall field of view, while the term "Bile Duct" may be used to obtain view 62. Adverbs, such as "slowly" can be added to modify a zoom-related command. For example, the command "Macro, slowly" may be used to instruct the system to progressively zoom out image-by-image at a preset rate to the overall field of view. Thus, the digital zoom capability of the present invention allows near instantaneous zooming of images, thus avoiding valuable time during surgery moving the scope around. The digital zoom feature further enables the surgeon to maintain a better sense of orientation within the field of surgery by allowing quick transitioning between views and by allowing zoomed views to be displayed within the general field of view. The digital zoom feature further is advantageous in that it enables a surgeon to control the zoom feature by spoken voice commands.

Thus, an endoscopic camera system having digital zoom operable in response to voice commands has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative sense rather than a restrictive sense.

What is claimed is:

1. A control unit for an endoscopic camera system, the control unit comprising:
    voice input means for receiving voice commands from a user;
    image input means for receiving image data from an endoscopic camera;
    image output means for outputting images to a display device; and
    processing means for processing the image data to generate images of internal features of a body, the processing means including zoom means for non-mechanically zooming the images, the zoom means including
        means for defining, in response to a set of voice commands from a user, zoomed views of a plurality of non-overlapping subsets of a field of view of the endoscopic camera for a particular position and orientation of the endoscopic camera,
        means for maintaining data identifying all of the zoomed views,
        means for using said data to select an appropriate one of said zoomed views in response to a first voice command specifying said zoomed view and for causing said zoomed view to be displayed on the display device in response to the first voice command, without requiring movement of the endoscopic camera, and
        means for switching between one of the zoomed views displayed on the display device to another one of the zoomed views displayed on the display device in response to a second voice command from the user, without requiring movement of the endoscopic camera.

2. A control unit as recited in claim 1, wherein the zoom means comprises means for digitally zooming the image in real-time.

3. A control unit as recited in claim 1, further comprising storage means for storing data, wherein the means for controlling the zoom means comprises means for storing in the storage means a plurality of zoom parameters defining at least one zoomed view in response to the signals representing voice commands.

4. A control unit as recited in claim 1, wherein the endoscopic camera system has a maximum field of view, the control unit further comprising means for causing the maximum field of view and a zoomed view representing a subset of the maximum field of view to be concurrently displayed on a display device.

5. A control unit as recited in claim 1, further comprising means for displaying a plurality of zoomed views of a feature in a sequence at a predefined rate in response to a single user input, each of the plurality of zoomed views showing the feature according to a different zoom factor.

6. An endoscopic camera system comprising:
    a scope;
    a camera head coupled to the scope;
    a transmission line coupled to the camera head; and
    a camera control unit coupled to the transmission line and configured to process the image data to generate an image, the camera control unit configured to output image data to display images on a display device, the camera control unit including a digital zoom unit configured to process the image data to zoom the image, wherein the camera control unit is further configured to
        define, in response to a set of voice commands from a user, zoomed views of a plurality of non-overlapping subsets of a field of view of the endoscopic camera for a particular position and orientation of the endoscopic camera,
        select an appropriate one of said zoomed views in response to a first voice command specifying said zoomed view and cause said zoomed view to be displayed on the display device in response to the first voice command, without requiring movement of the endoscopic camera, and
        switch between one of the zoomed views displayed on the display device to another one of the zoomed views displayed on the display device in response to a second voice command from the user, without requiring movement of the endoscopic camera.

7. An endoscopic camera system as recited in claim 6, wherein the zoom unit is configured to provide real-time zooming.

8. An endoscopic camera system as recited in claim 7, wherein the endoscopic camera system has a maximum field of view, wherein the zoom unit is configured to generate a zoomed view of a subset of the maximum field of view, and wherein the camera control unit is configured to cause the maximum field of view and the zoomed view to be displayed on a display device concurrently.

9. An endoscopic camera system as recited in claim 6, further comprising:
    an audio input device; and
    a voice control unit coupled to the camera control unit and the audio input device, the voice control unit configured to control the zoom unit in response to voice commands input through the audio input device.

10. An endoscopic camera system as recited in claim 9, further comprising a memory, wherein the voice control unit is further configured to cooperate with the camera control unit to store parameters defining at least one zoomed view in response to voice commands input through the audio input device, the defined zoom view selectable in response to a user input.

11. An endoscopic camera system as recited in claim 10, wherein the voice control unit is further configured to cooperate with the camera control unit to cause the defined zoomed view to be displayed on a display device in response to voice commands input through the audio input device.

12. An endoscopic camera system comprising:
    a scope for insertion into a body;
    a light source optically coupled to the scope;
    a camera head coupled to the scope, the camera head including video circuitry for acquiring video image data of internal features of the body;
    a camera control unit coupled to the scope and configured to process the video image data to generate video images, the camera control unit including zoom circuitry configured to further process the data to digitally zoom the images in real-time;
    a display device coupled to the camera control unit for displaying the images in real-time;
    an audio input device; and
    a voice control unit coupled to the camera control unit and coupled to receive voice commands input to the audio input device, the voice control unit configured to cooperate with the camera control unit to operate the zoom circuitry in response to the voice commands, wherein the camera control unit is configured to
        define, in response to a set of voice commands from a user, zoomed views of a plurality of non-overlapping subsets of a field of view of the endoscopic camera for a particular position and orientation of the endoscopic camera, select an appropriate one of said zoomed views in response to a first voice command specifying said zoomed view and cause said zoomed view to be displayed on the display device in response to the first voice command, without requiring movement of the endoscopic camera, and switch between one of the zoomed views displayed on the display device to another one of the zoomed views displayed on the display device in response to a second voice command from the user, without requiring movement of the endoscopic camera.

13. An endoscopic camera system as recited in claim 12, wherein the voice control unit is further configured to respond to voice commands input to the audio input device by cooperating with the camera control unit to store parameters defining a plurality of selectable zoomed views.

14. An endoscopic camera system as recited in claim 13, wherein the voice control unit is further configured to respond to a voice command input to the audio input device by cooperating with the camera control unit to select one of the zoomed views.

15. An endoscopic camera system as recited in claim 13, wherein the camera control unit is configured to concurrently display the views of the non-overlapping subsets of the maximum field of view on a display device.

16. An endoscopic camera system as recited in claim 12, wherein the camera control unit is further configured to cause a plurality of zoomed views of a feature to be displayed in a sequence at a predefined rate in response to a single user input, each of the plurality of zoomed views showing the feature according to a different zoom factor.

17. A method of operating an endoscopic camera system, the method comprising:

acquiring video image data of internal features of a body from an endoscopic camera;

processing the video image data to generate an image for display by a display device;

in response to a user input, non-mechanically zooming the image;

receiving voice commands from a user for controlling functions of the endoscopic camera system, including said zooming;

defining, in response to a set of voice commands from a user, zoomed views of a plurality of non-overlapping subsets of a field of view of the endoscopic camera for a particular position and orientation of the endoscopic camera;

maintaining data identifying all of the zoomed views;

using said data to select an appropriate one of said zoomed views in response to a first voice command specifying said zoomed view and for causing said zoomed view to be displayed on the display device in response to the first voice command, without requiring movement of the endoscopic camera; and switching between one of the zoomed views displayed on the display device to another one of the zoomed views displayed on the display device in response to a second voice command from the user, without requiring movement of the endoscopic camera.

18. A method as recited in claim 17, wherein said zooming comprises zooming the image in real-time.

19. A method as recited in claim 17, further comprising executing a speech recognition process of the endoscopic camera system to recognize the voice commands.

20. A method as recited in claim 19, further comprising:
receiving a set of voice commands; and
automatically storing, in a storage device of the endoscopic camera system, information defining a plurality of zoom settings in response to the set of voice commands.

21. A method as recited in claim 17, wherein the endoscopic camera system has a maximum field of view, the method further comprising causing the maximum field of view and a zoomed view representing a subset of the maximum field of view to be concurrently displayed on a display device.

22. A method as recited in claim 17, further comprising causing a plurality of zoomed views of a feature to be displayed in a sequence at a predefined rate in response to a single user input, each of the plurality of zoomed views showing the feature according to a different zoom factor.

* * * * *